(12) United States Patent
Scott

(10) Patent No.: US 7,862,528 B2
(45) Date of Patent: Jan. 4, 2011

(54) PATELLA STABILIZING METHOD AND SYSTEM

(75) Inventor: John Scott, Dallas, TX (US)

(73) Assignee: New Options Sports, Dallas, TX (US)

( * ) Notice: Subject to any disclaimer, the term of this patent is extended or adjusted under 35 U.S.C. 154(b) by 61 days.

(21) Appl. No.: 12/037,320

(22) Filed: Feb. 26, 2008

(65) Prior Publication Data
US 2008/0300524 A1 Dec. 4, 2008

Related U.S. Application Data

(60) Provisional application No. 60/904,444, filed on Feb. 28, 2007.

(51) Int. Cl.
*A61F 5/00* (2006.01)
(52) U.S. Cl. .......................... 602/23; 602/26
(58) Field of Classification Search ............ 602/16, 602/23, 26–27, 60–63; 128/882
See application file for complete search history.

(56) References Cited

U.S. PATENT DOCUMENTS

| | | | |
|---|---|---|---|
| 4,494,534 A | 1/1985 | Hutson | |
| 4,856,501 A | 8/1989 | Castillo et al. | |
| 4,873,967 A | 10/1989 | Sutherland | |
| 4,986,264 A | 1/1991 | Miller | |
| 5,024,216 A * | 6/1991 | Shiono | 602/26 |
| 5,277,697 A * | 1/1994 | France et al. | 602/16 |
| 5,554,104 A | 9/1996 | Grim | |
| 5,562,605 A | 10/1996 | Taylor et al. | |
| 5,624,389 A | 4/1997 | Zepf | |
| 5,807,298 A * | 9/1998 | Palumbo | 602/62 |
| 5,810,752 A | 9/1998 | Grifka | |
| 5,873,848 A * | 2/1999 | Fulkerson | 602/62 |
| 5,921,946 A | 7/1999 | Tillinghast et al. | |
| 6,066,110 A | 5/2000 | Nauert | |
| 6,287,269 B1 * | 9/2001 | Osti et al. | 602/62 |
| 7,060,045 B2 * | 6/2006 | Mason et al. | 602/5 |

* cited by examiner

*Primary Examiner*—Michael A. Brown
(74) *Attorney, Agent, or Firm*—Winstead PC

(57) ABSTRACT

A unitary knee patella stabilizer for a user's leg, the stabilizer including a patella stabilizer sleeve having an open-upper end and an open-lower end adapted to slidably receive the leg portion of the user and an upper fastener assembly having a first strap, connected at its proximal end to an upper end of the patella stabilizer sleeve, the first strap having a fastener at a distal end of the first strap. The apparatus further includes a lower fastener assembly having a second strap, connected at its proximal end to a lower end of the patella stabilizer sleeve, the second strap having a fastener at a distal end of the second strap and a buttress comprising a plurality of straps adapted to be adjustably positioned on an inside surface of the patella stabilizer sleeve around a location on a circumferential edge of a patella opening.

13 Claims, 7 Drawing Sheets

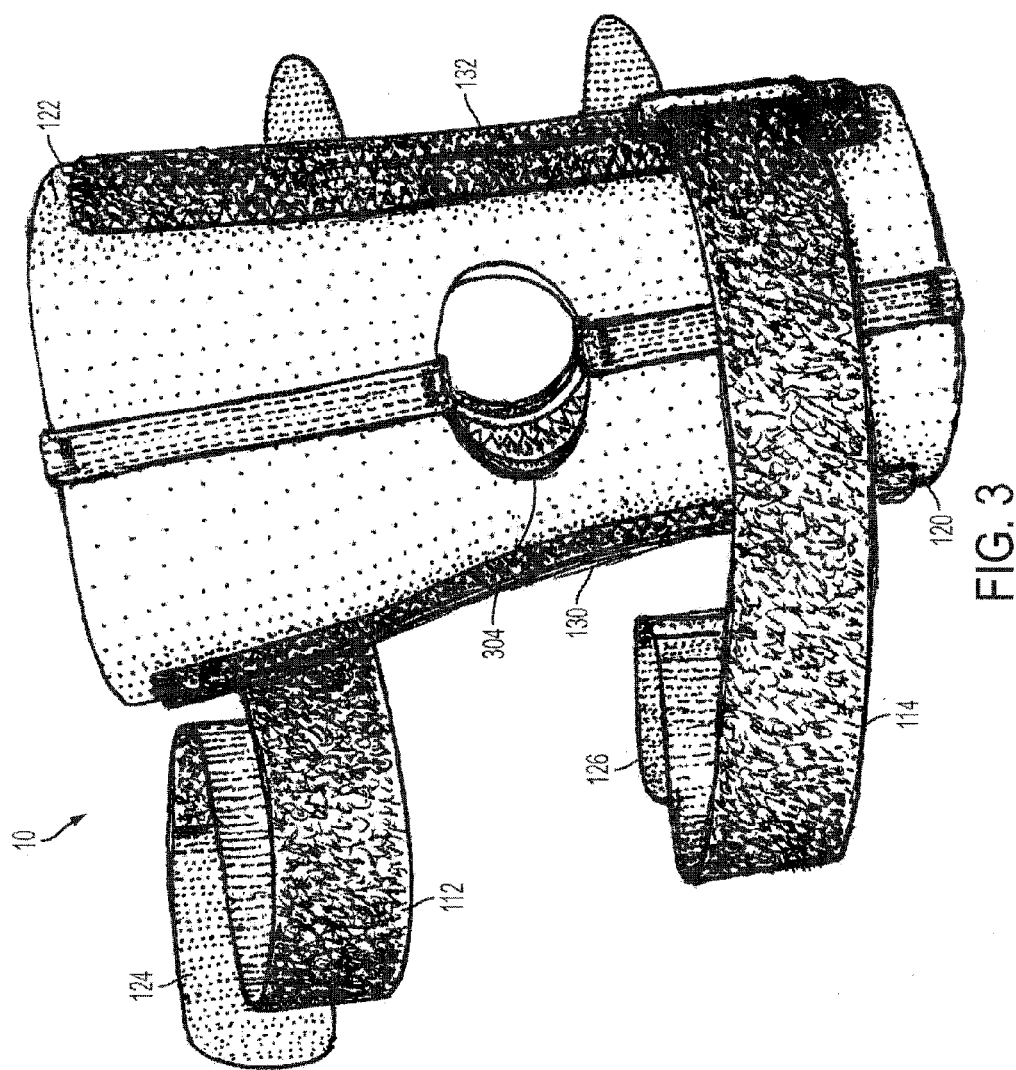

TOP VIEW

BOTTOM VIEW

PATELLA STABILIZING METHOD AND SYSTEM

CROSS-REFERENCE TO RELATED APPLICATIONS

This application claims priority from and incorporates by reference the entire disclosure of U.S. Provisional Patent Application No. 60/904,444, which was filed on Feb. 28, 2007.

BACKGROUND OF THE INVENTION

1. Field of Invention

The present invention relates to orthopedic joint supports and, more particularly, but not by way of limitation, to an orthopedic support, system and method for supporting a knee with a buttress adapted to be adjustably positioned for proper alignment with a user's patella.

2. History of Related Art

It is common in the Sports Medicine Industry to utilize orthopedic supports for various body parts subject to injury. The most common support areas include the knees, elbows, and ankles. Often injuries to these areas of the body can be treated by the utilization of the appropriate orthopedic support. In the event of surgery, rehabilitation is sometimes augmented by the utilization of such supports.

The design of orthopedic supports has changed considerably over the past two decades. The types of material used as well as the fastening an hinging mechanisms associated with orthopedic supports have been the subject of considerable study and improvement. U.S. Pat. No. 4,986,264 to Miller, teaches a knee brace having an interior tibial shell and an interior femoral which are closely configured to the shape of the lower leg and thigh respectively and which are joined by a frame in the form of a pair of polycentric hinge joints. U.S. Pat. No. 4,856,501 to Castillo et. al. teaches a knee brace having adjustable width frame pivoted to cuffs. The brace as set forth therein includes first and second frame members disposed on opposite sides of the joint to be supported, and first and second hinge members disposed substantially adjacent to joint and connected to the frame members to pivot the frame members about the joint.

Another example of related art is shown in U.S. Pat. No. 4,494,534 to Hudson. This patent teaches a universal leg brace system for controlling the degree of motion permitted by wearer's knee characterized by respective flexible sheets of cushioned material adapted for snugly wrapping around the wearer's thigh and calf. U.S. Pat. No. 5,554,104 to Grim likewise teaches a custom formed knee brace. This brace is taught to support weakened or injured knees by having formed components which conform to the unique configuration of an individual's leg surfaces. Other references include U.S. Pat. No. 6,066,110 to Nauert; U.S. Pat. No. 5,810,752 to Grifka; U.S. Pat. No. 5,624,389 to Zepf; U.S. Pat. No. 4,873,967 to Sutherland; U.S. Pat. No. 5,921,946 to Tillinghast; and U.S. Pat. No. 5,562,605 to Taylor.

As seen from the patents listed above, the aspect of joint support, flexibility, and rehabilitation have received considerable attention in prior orthopedic support design. One area of continued concern is, however, the adaptability of a single orthopedic support for a knee that is adapted to provide a desired pressure on the user's knee in order to properly align and support a user's patella.

For the aforementioned reasons, there is a need in the art for an orthopedic support, system and method for a knee that overcomes these limitations to provide a new level of flexibility and customizability.

SUMMARY OF THE INVENTION

The present invention relates to orthopedic joint supports. More particularly, one aspect includes a unitary patella stabilizer for a user's leg. The stabilizer includes a patella stabilizer sleeve having an open-upper end and an open-lower end adapted to slidably receive the leg portion of the user and an upper fastener assembly having a first strap, connected at its proximal end to an upper end of the patella stabilizer sleeve, the first strap having a fastener at a distal end of the first strap. The apparatus further includes a lower fastener assembly having a second strap, connected at its proximal end to a lower end of the patella stabilizer sleeve, the second strap having a fastener at a distal end of the second strap and a buttress comprising a plurality of straps adapted to be adjustably positioned on an inside surface of the patella stabilizer sleeve around a location on a circumferential edge of a patella opening.

According to exemplary embodiment, a unitary hinged knee support apparatus adapted to accommodate a leg portion of a user includes an open-upper end and an open-lower end, a patella opening, and an upper fastener assembly having a first strap, connected at its proximal end to an upper end of the apparatus, the first strap having a fastener at a distal end of the first strap. The apparatus further includes a lower fastener assembly having a second strap, connected at its proximal end to a lower end of the apparatus, the second strap having a fastener at a distal end of the second strap, the apparatus adapted to receive a buttress comprising a plurality of straps, the buttress being adapted to be adjustably positioned on an inside surface of the apparatus around a location on a circumferential edge of the patella opening.

According to another exemplary embodiment, a method for properly aligning a user's patella includes providing a unitary knee patella stabilizer having an upper fastener assembly comprising a first strap and a lower fastener assembly comprising a second strap and inserting a leg portion of the user through an open-upper end and an open-lower end of the stabilizer. The method further includes securing, via the upper fastener assembly, a thigh region of the user, securing, via the lower fastener assembly, a calf region of the user, and adjustably positioning, on an inside surface of the device around a location on a circumferential edge of a patella opening, a buttress comprising a plurality of straps for varying compression around the user's patella by increasing or decreasing tightness of the plurality of straps.

BRIEF DESCRIPTION OF THE DRAWINGS

A more complete understanding of the system of the present invention may be obtained by reference to the following Detailed Description when taken in conjunction with the accompanying Drawings wherein:

FIG. 3 is a back view of the exemplary configuration of the patella stabilizer sleeve in accordance with an embodiment of the present invention;

DETAILED DESCRIPTION OF THE INVENTION

Figure 1:
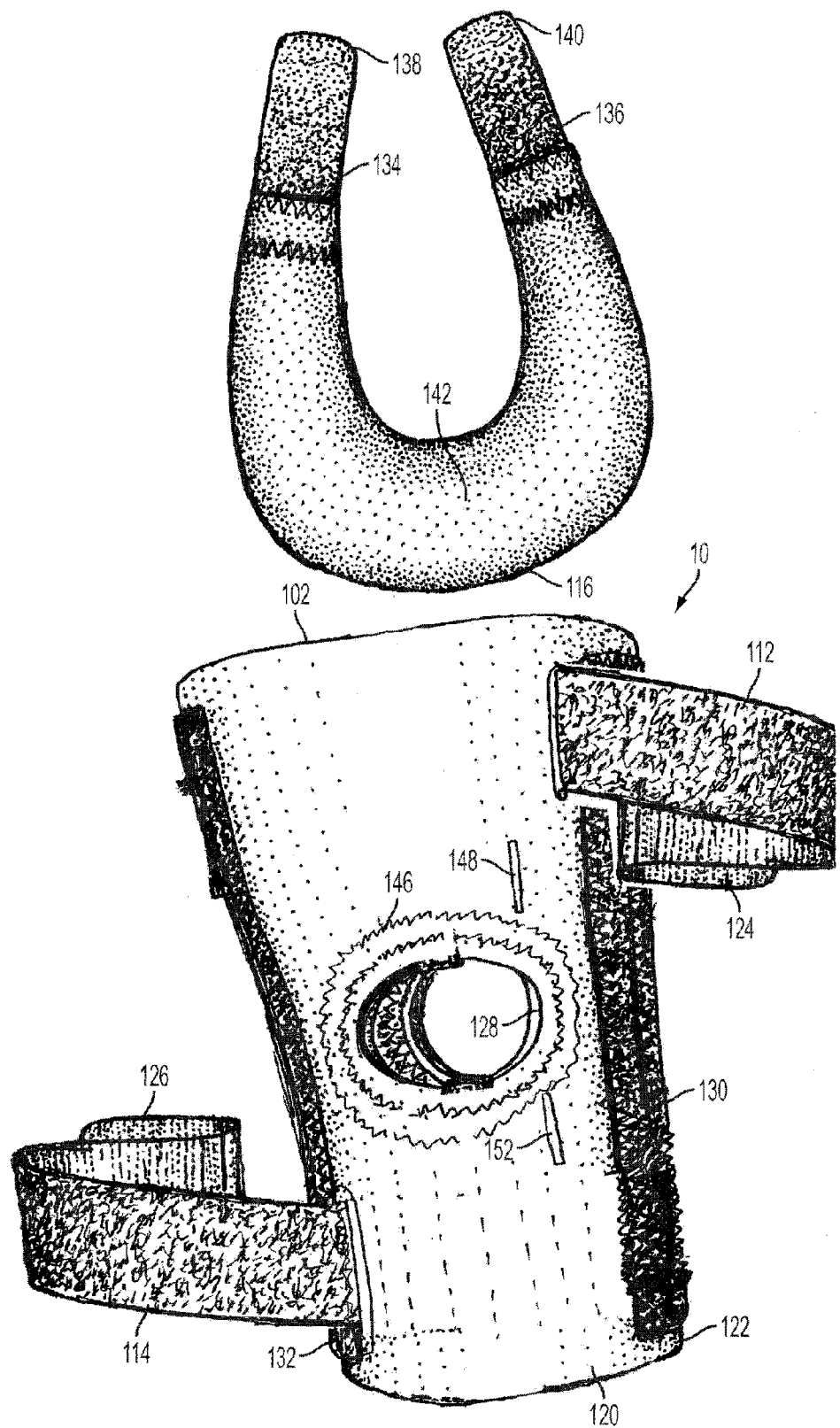
FIG. 1 is a front view of elements of a patella stabilizer system in accordance with a preferred embodiment of the present invention.

In the following detailed description, reference is made to the accompanying drawings that show, by way of illustration, specific embodiments in which the invention may be practiced. These embodiments are described in sufficient detail to enable those skilled in the art to practice the invention. It is to be understood that the various embodiments of the invention, although different, are not necessarily mutually exclusive. For example, a particular feature, structure, or characteristic described herein in connection with one embodiment may be implemented within other embodiments without departing from the spirit and scope of the invention. In addition, it is to be understood that the location or arrangement of individual elements within each disclosed embodiment may be modified without departing from the spirit and scope of the invention. The following detailed description is, therefore, not to be taken in a limiting sense, and the scope of the present invention is defined only by the appended claims, appropriately interpreted, along with the full range of equivalents to which the claims are entitled. In the drawings, like numerals refer to the same or similar functionality throughout the several views.

Referring first to FIG. 1, there is shown a preferred embodiment of a patella stabilizer system 100 of the present invention. The patella stabilizer system 100 comprises a patella stabilizer sleeve 10, an upper fastener assembly having a strap 112, a lower fastener assembly having a strap 114, and a patella support buttress 116. While only two straps are shown in FIG. 1, it will be understood to one of ordinary skill in the art that any number of straps may be used without departing from the spirit and scope of the present invention. The patella stabilizer sleeve 10 is constructed using any natural or synthetic material, including both inelastic and elastic materials, having sufficient flexibility and resiliency to enable the patella stabilizer sleeve 10 to anatomically conform to the body member to which it is applied. For example, the patella stabilizer sleeve 10 may be formed of, for example, two-sided nylon Neoprene, which provides durability and elasticity. The two-sided nylon Neoprene allows the patella stabilizer sleeve 10 to be easily slipped onto a user leg and more particularly the knee area. According to an exemplary embodiment, the two-sided nylon Neoprene has an approximate thickness between 1/8 to 3/16 inch. The outside, comprising a front side 120 and a back side 122, is constructed of UBL, which is standard and well known in the art. The body of straps 112 and 114, with the exception of fasteners 124 and 126 may be constructed with hook a pile portions to facilitate adjustability and ease of use by user.

Still referring to FIG. 1, the patella stabilizer sleeve 10 includes a large patella opening 128 for added comfort, an open upper-end 102, and an open lower-end 104, and a popliteal opening 304 opposite the patella opening 128 (shown in FIG. 3). As described below, the upper fastener assembly and the lower fastener assembly having straps 112, 114 may be constructed with hook and pile portions to facilitate adjustability and ease of use by the user. Once the patella stabilizer sleeve 10 is slipped onto a users leg and more particularly the knee area, the straps 112, 114 are wrapped around a thigh and calf regions of the user. The lengths of the straps 112, 114 are preferably sufficient to encompass the thigh and calf regions at least once. It will be appreciated that compression may be adjusted to a desired level by increasing or decreasing the tightness of the straps 112 and 114 around the thigh and calf regions. Still referring to FIG. 1, an internal hinge 122 is distinctly placed along a medial portion of the patella stabilizer sleeve 10. According to an exemplary embodiment, the internal hinge 122 may be either a polycentric (double axis) hinge, a single axis hinge, a complex hinge, or a spiral stay. Other types of hinges may also be used as will be shown in more detail below. A second hinge 132 is disposed opposite hinge 122, and is positioned on the outside portion of the knee to balance the support about the knee. Stitching 144 is shown on the strap 112 as well as stitching 146 shown around the patella opening 128. This stitching is shown for purposes of illustration only, and other stitching embodiments may be incorporated herein. All illustrations thereof should not be deemed limited in any respect relative to the principles of the present invention.

Still referring to FIG. 1, the patella stabilizer system 100 further includes a patella support buttress 116. The buttress 116 comprises a plurality of straps 134 and 136. The body of straps 134 and 136, with the exception of fasteners 138 and 140 may be constructed with hook and pile portions to facilitate adjustability. The buttress 116 includes a front side 142 and a back side 144 (shown in FIG. 4B). According to an exemplary embodiment, the front side 142 is made of a material that has grip characteristics and prevents slippage when placed against human skin such as, for example, shark-skin. The back side 144 of the buttress 116 may be constructed with hook and pile portions to facilitate adjustability and ease of use by the user. The buttress 116 is adapted to be placed on an inside surface of the patella stabilizer sleeve 10 around a location on a circumferential edge of the patella opening 128.

The patella stabilizer sleeve 10 includes four slots 148, 150, 152, 154 (shown in FIG. 6) around the patella opening 128. The slots 148, 150, 152, 154 (FIG. 6) are adapted to allow passage of the buttress straps 134 and 136 for securement of the buttress 116 to the patella stabilizer sleeve 10. According to an exemplary embodiment, the inside surface of the patella stabilizer sleeve 10 around the circumferential edge of the patella opening 128 may be constructed with hook and pile portions to engage the buttress 116 in order to facilitate adjustability of the buttress 116. The buttress 116 may be adjustably positioned on the inside surface of the patella stabilizer sleeve 10 around a location on the circumferential edge of the patella opening 128 to provide a desired pressure and properly align a user's patella. According to an exemplary embodiment, the buttress 116 can be positioned in a medial or lateral direction relative to the user's patella.

Figure 2:
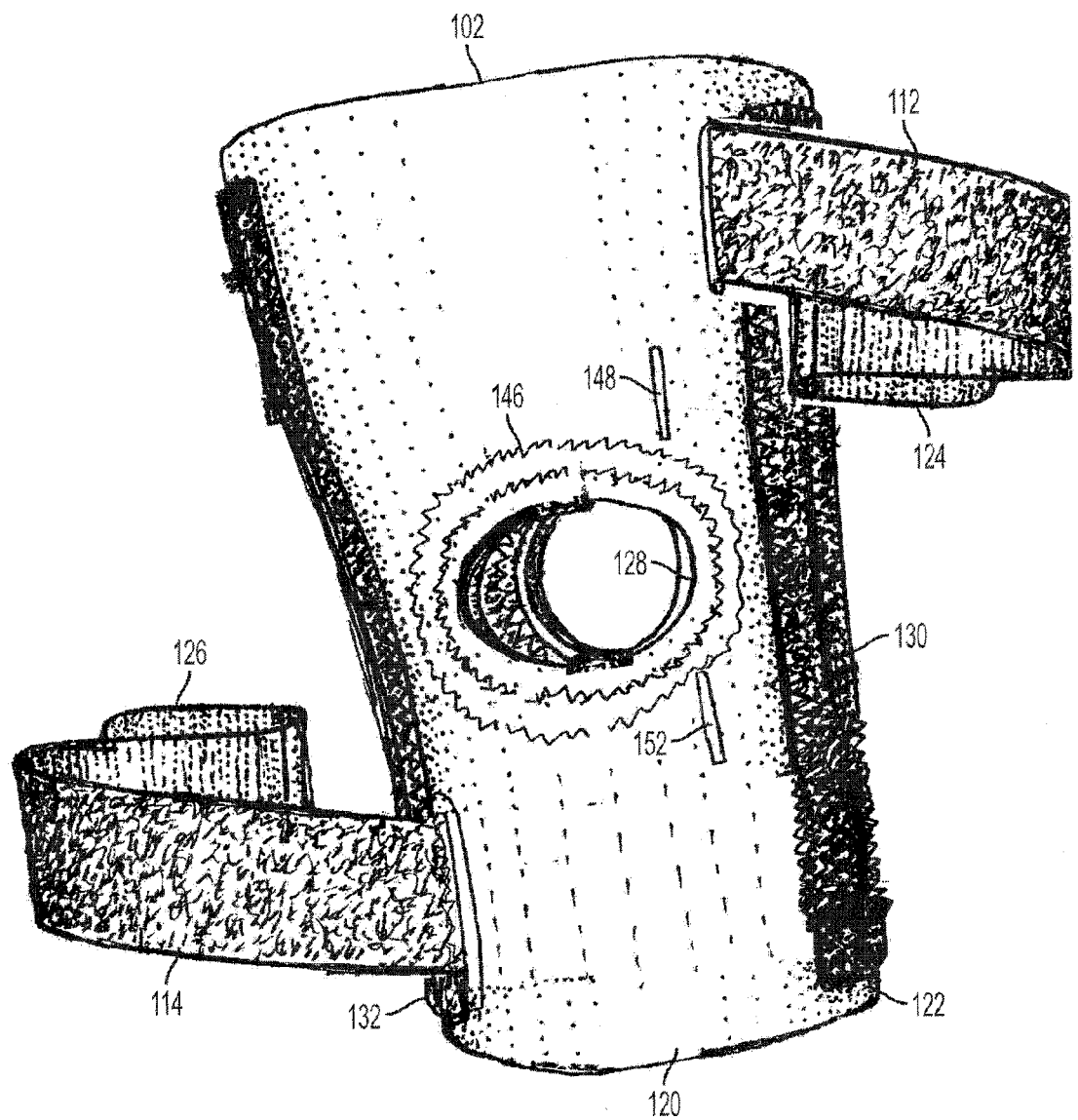
FIG. 2 is a front view of an exemplary configuration of a patella stabilizer sleeve in accordance with an embodiment of the present invention.

FIG. 2 is a front view of an exemplary configuration of a patella stabilizer sleeve 10 in accordance with an embodiment of the present invention. Details of the patella stabilizer sleeve 10 have been disclosed with respect to FIG. 1 above.

FIG. 3 is a back view of an exemplary configuration of the patella stabilizer sleeve 10 in accordance with an embodiment of the present invention. The patella stabilizer sleeve 10 further includes a popliteal opening 304 opposite the patella opening 128 for added comfort. It is important to note that FIGS. 1-3 and the description herein are directed to a universal patella stabilizer sleeve 10 adapted to properly align a user's patella and can be worn interchangeably on the left and the right knee of the user.

Figure 4B:
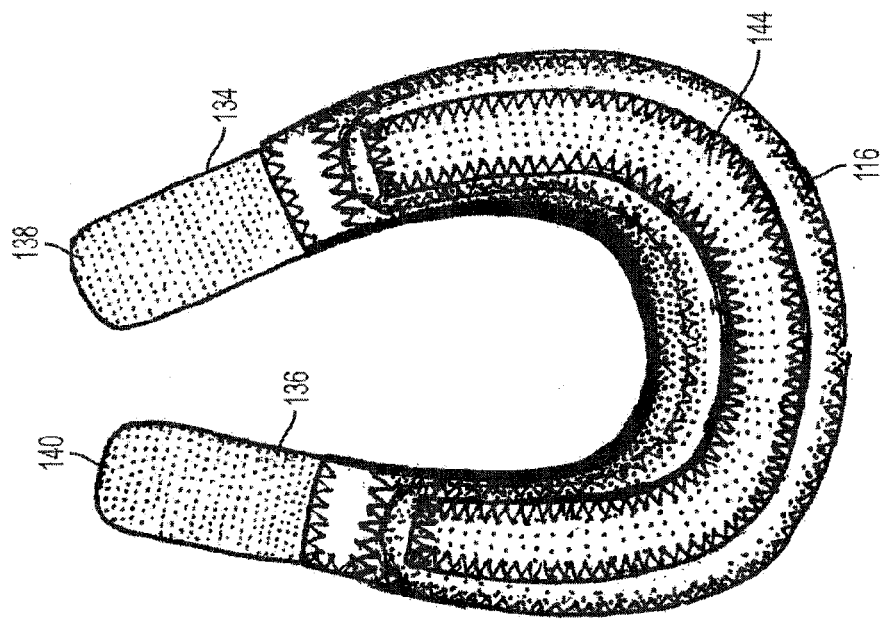
FIG. 4B is a back view of a buttress of the patella stabilizer system in accordance with a preferred embodiment of the present invention.
Figure 4A:
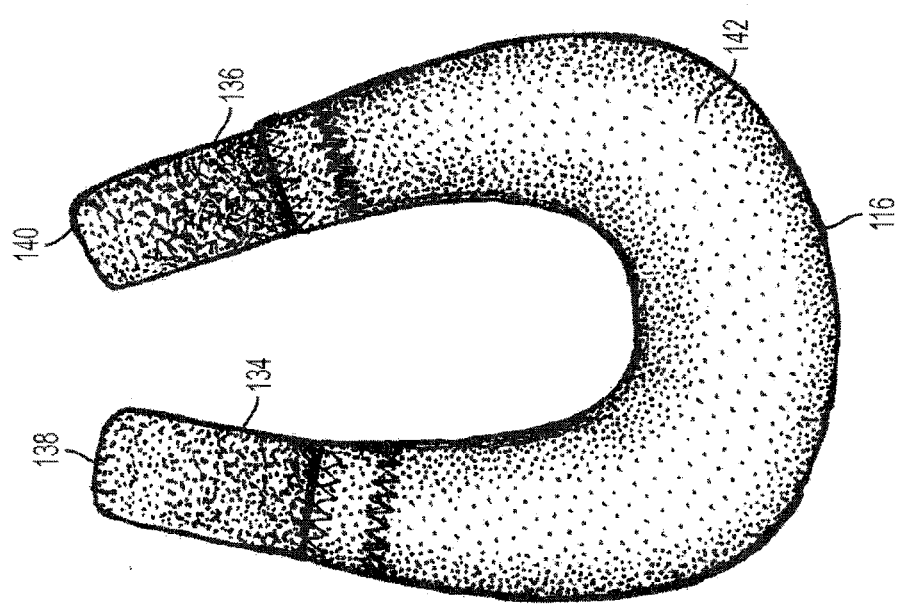
FIG. 4A is a front view of a buttress of the patella stabilizer system in accordance with a preferred embodiment of the present invention.

FIGS. 4A-4B illustrate front and back views of a buttress 116 of the patella stabilizer system 100 in accordance with a preferred embodiment of the present invention. The buttress 116 comprises a plurality of straps 134, 136. The body of straps 134 and 136, with the exception of fasteners 138 and 140 may be constructed with hook and pile portions to facilitate adjustability and ease of use by the user. The buttress 116 includes a front side 142 (illustrated in FIG. 4A) and a back side 144 (illustrated in FIG. 4B). According to an exemplary embodiment, the front side 142 is made of a material that has grip characteristics and prevents slippage when placed against human skin such as, for example, shark-skin. The back side 144 of the buttress 116 may be constructed with hook and pile portions to facilitate adjustability and ease of use by the user. The buttress 116 is adapted to be placed on an inside surface of the patella stabilizer sleeve 10 around a location on a circumferential edge of the patella opening 128. According to an exemplary embodiment, the buttress 116 is horse-shoe like in shape. However, the buttress 116 may be of other shapes such that the buttress 116 can be placed on an inside surface of the patella stabilizer sleeve 10 around a location on a circumferential edge of the patella opening 128 to provide a desired pressure and properly align the user's patella.

Figure 5A:
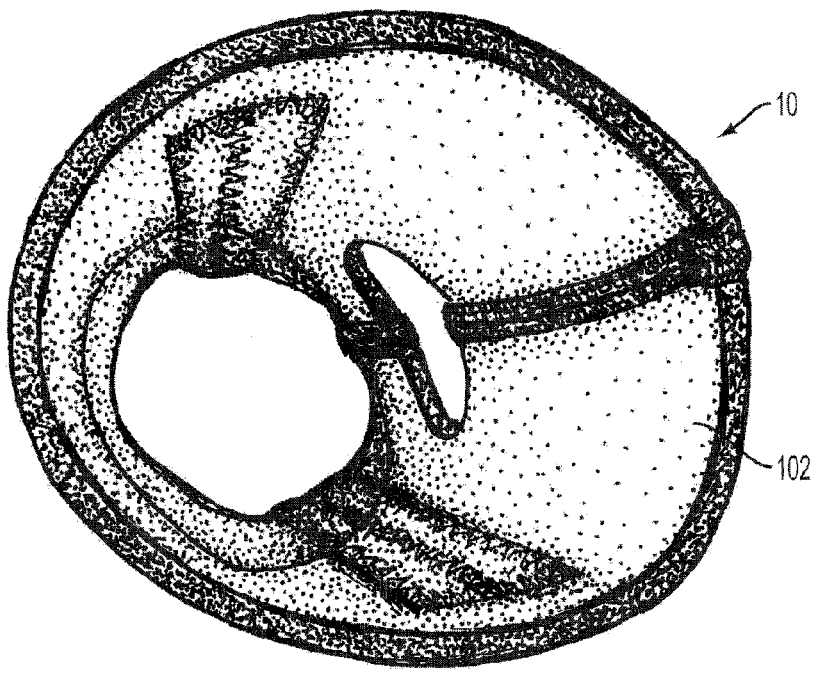
FIG. 5A is a top view of the exemplary configuration of the patella stabilizer sleeve in accordance with an embodiment of the present invention.
Figure 5B:
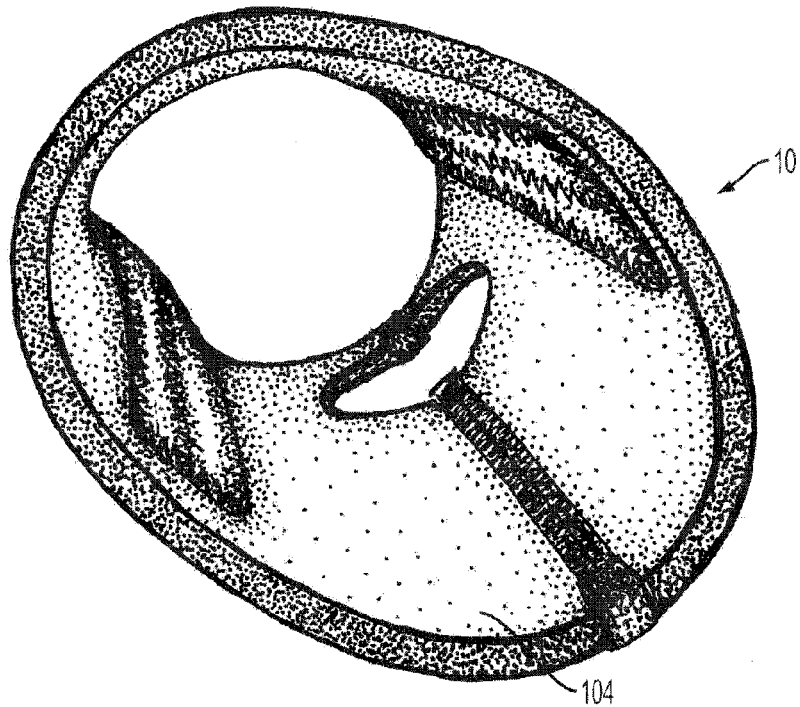
FIG. 5B is a bottom view of the exemplary configuration of the patella stabilizer sleeve in accordance with an embodiment of the present invention.

FIGS. 5A-5B illustrate top and bottom views of the exemplary configuration of the patella stabilizer in accordance with an embodiment of the present invention.

Figure 6:
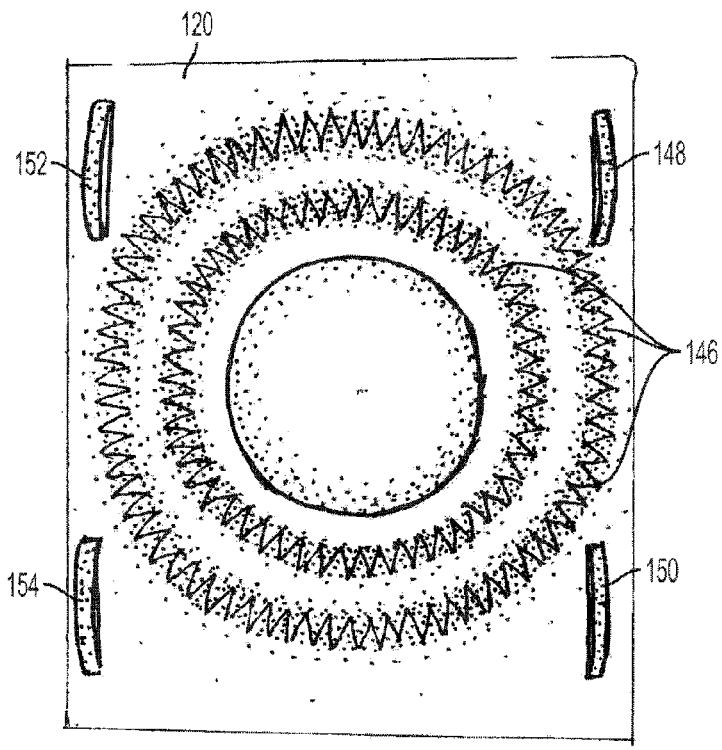
FIG. 6 is an illustration of a close up view of a patella opening of the patella stabilizer sleeve in accordance with an embodiment of the present invention.

FIG. 6 is an illustration of a close up view of a patella opening 128 of the patella stabilizer sleeve 10 in accordance with an embodiment of the present invention. The patella stabilizer sleeve 10 includes a large patella opening 128. The patella stabilizer sleeve 10 further includes four slots 148, 150, 152, 154 around the patella opening 128. The slots 148, 150, 152, 154 are adapted to allow passage of the buttress straps 134, 136 for securement of the buttress 116 to the patella stabilizer sleeve 10. According to an exemplary embodiment, the inside surface of the patella stabilizer sleeve 10 around the circumferential edge of the patella opening 128 may be constructed with hook and pile portions to engage and facilitate adjustability of the buttress 116. According to an exemplary embodiment, the front side 142 of the buttress 116 is made of a material that has grip characteristics and prevents slippage when placed against human skin such as, for example, shark-skin. The back side 144 of the buttress 116 may be constructed with hook and pile portions to engage with the hook and pile portions on an inside surface of the patella stabilizer sleeve 10 around the circumferential edge of the patella opening 128. The buttress 116 is adapted to be placed on an inside surface of the patella stabilizer sleeve 10 around a location on a circumferential edge of the patella opening 128. The buttress 116 may be adjustably positioned on the inside surface of the patella stabilizer sleeve 10 around a location on the circumferential edge of the patella opening 128 to provide a desired pressure and properly align a user's patella. According to an exemplary embodiment, the buttress 116 can be positioned in a medial or lateral direction relative to the user's patella.

Figure 7:
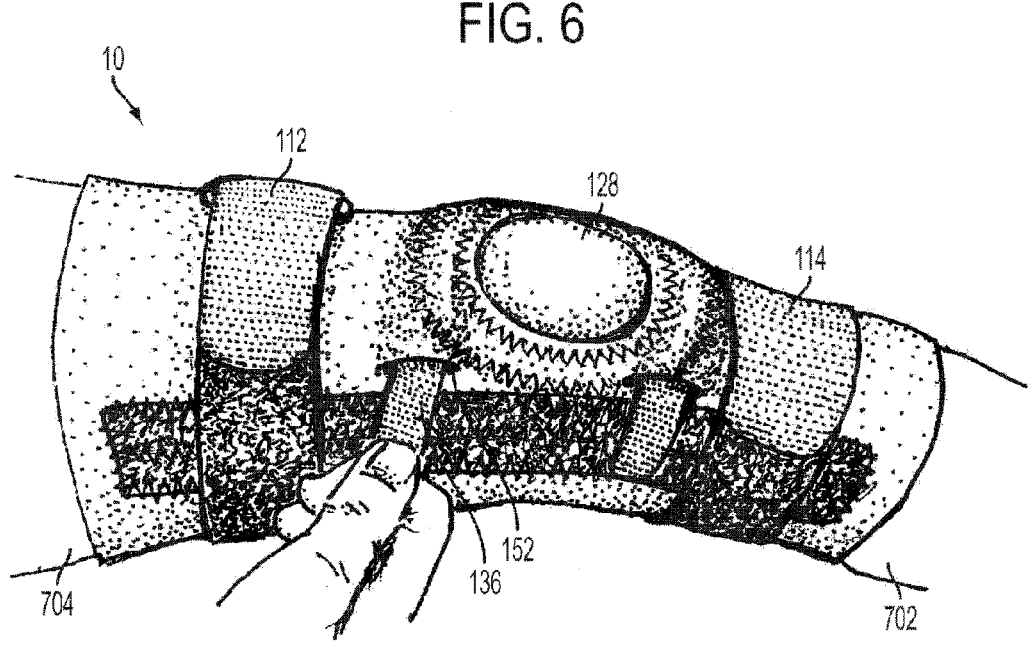
FIG. 7 is a perspective view of a patella stabilizer sleeve placed on a user's leg in accordance with an embodiment of the present invention.

FIG. 7 is a perspective view of a patella stabilizer sleeve 10 and the buttress 116 placed on a user's leg in accordance with an embodiment of the present invention. The patella stabilizer sleeve 10 is adapted to be slipped onto the user's leg such that the lower strap 114 is adapted to secure a calf region 702 of the user while the upper strap 112 is adapted to secure a thigh region 704 of the user. FIG. 7 further illustrates the slot 152 which allows passage of the buttress straps 136 for securement of the buttress 116 to the patella stabilizer sleeve 10. The buttress 116 is adapted to be placed on an inside surface of the patella stabilizer sleeve 10 around a location on a circumferential edge of the patella opening 128. The buttress 116 may be adjustably positioned on the inside surface of the patella stabilizer sleeve 10 around a location on the circumferential edge of the patella opening 128 to properly align a user's patella. According to an exemplary embodiment, the buttress 116 can be positioned in a medial or lateral direction relative to the user's patella. One advantage of the present invention is that the buttress 116, which is adapted to be adjustably positioned on the inside surface of the patella stabilizer sleeve 10 around a location on the circumferential edge of the patella opening 128, is adapted to properly align a user's patella.

Figure 8:
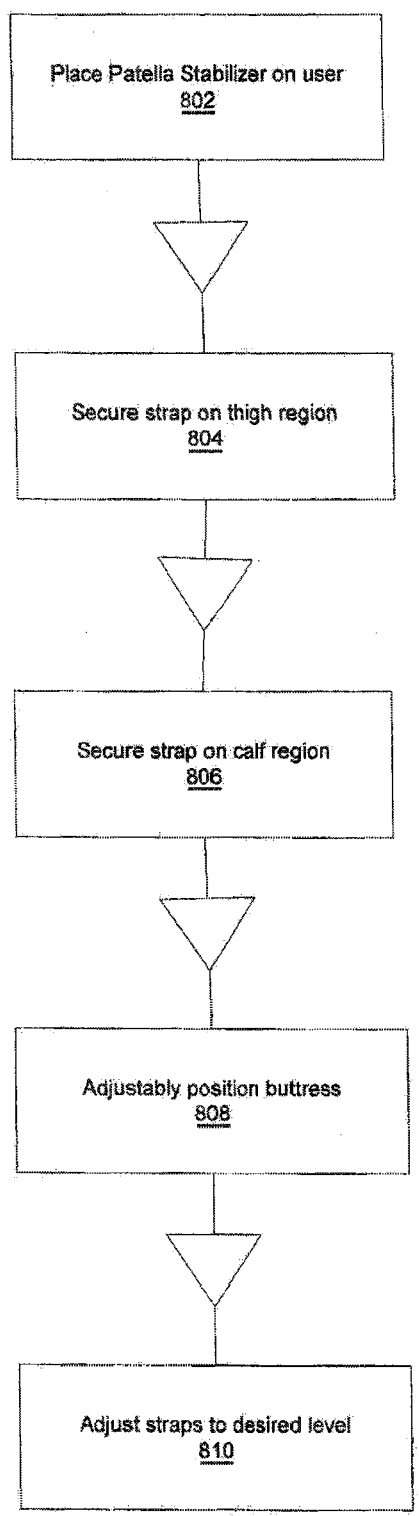
FIG. 8 is a flow diagram illustrating a method for using the patella stabilizer system in accordance with an embodiment of the present invention.

Referring now to FIG. 8, there is shown a flow diagram illustrating a method 800 for using the patella stabilizer sleeve 10 according to an embodiment of the present invention. At step 802, the user slips the patella stabilizer sleeve 10 onto the user leg and more particularly the knee area through the open upper-end 102 of the patella stabilizer system 100. At step 804, the strap 112 of the upper fastener assembly is secured about the thigh region of the user. At step 806, the strap 114 of the lower fastener assembly is secured about the calf region of the user. In step 808, the buttress 116 is adjustably positioned on the inside surface of the patella stabilizer sleeve 10 around a location on the circumferential edge of the patella opening 128 to provide a desired pressure and properly align a user's patella. According to an exemplary embodiment, the buttress 116 can be positioned in a medial or lateral direction relative to the user's patella. At step 810, the straps 112, 114, 134, and 136 are adjusted to a desired level by increasing or decreasing the tightness of the straps 112, 114, 134, and 136 around the thigh region, the calf region and the patella region, respectively.

It should be noted that the term "hook and pile fasteners" is a recognized structure to one skilled in the art and is often sold under the trademark Velcro®. It is well known that the hook and pile material engage one another. In addition, various surface designs, patterns, and colors may be used as well as various thicknesses of neoprene. Likewise, the present invention is not limited to the use of neoprene as other materials may prove satisfactory in their use as patella stabilizers. The size and shape of the patella stabilizer sleeve 10 along with the buttress 116 as shown herein is an exemplary embodiment and other cutout shapes and clearance designs may be utilized in order to accommodate various leg sizes.

Although various embodiments of the patella stabilizer system of the present invention have been illustrated in the accompanying Drawings and described in the foregoing Detailed Description, it will be understood that the invention is not limited to the embodiments disclosed, but is capable of numerous rearrangements, modifications, and substitutions without departing from the spirit of the invention as set forth herein.

What is claimed is:

1. A unitary knee patella stabilizer for a user's leg, the stabilizer comprising:
- a patella stabilizer sleeve having an open-upper end and an open-lower end adapted to slidably receive the leg portion of the user;
- an upper fastener assembly having a first strap, connected at its proximal end to an upper end of the patella stabilizer sleeve, the first strap having a fastener at a distal end of the first strap;
- a lower fastener assembly having a second strap, connected at its proximal end to a lower end of the patella stabilizer sleeve, the second strap having a fastener at a distal end of the second strap;
- a buttress comprising an upper strap and a lower strap adapted to be adjustably positioned on an inside surface of the patella stabilizer sleeve around a location on a circumferential edge of a patella opening;
- a first pair of slots positioned proximate to an interior aspect of the patella opening;
- a second pair of slots positioned proximate to an exterior aspect of the patella opening; and
- wherein the first and second pairs of slots are adapted to allow passage of the plurality of buttress straps therethrough for securement of the buttress to the patella stabilizer sleeve thereby allowing positioning of the buttress in at least one of a medial or a lateral direction relative to a user's patella.

2. The system of claim 1, wherein the upper and lower buttress straps are adapted to properly align a user's patella by allowing parallel passage of the upper and lower buttress straps through the pair of slots around the patella opening such that the buttress and the upper and lower buttress straps form a C-shape structure for providing stability and proper alignment of the user's patella.

3. The system of claim 1, wherein the upper and lower buttress straps are adapted to vary compression around the user's patella by allowing an angular passage of the upper and lower buttress straps through the pair of slots around the patella opening such that when the upper and lower buttress straps are pulled in an upward and downward criss-cross manner, the upper and lower buttress straps move closer and reduce a radius of the buttress.

4. The system of claim 1, wherein an inside surface of the patella stabilizer sleeve around a location on a circumferential edge of the patella opening is constructed of hook and pile portions to engage and facilitate adjustability of the buttress.

5. The system of claim 1, wherein a back side of the buttress is constructed of hook and pile portions to engage with hook and pile portions on the inside surface of the patella stabilizer sleeve around the location on the circumferential edge of the patella opening.

6. The system of claim 1, wherein the buttress is positioned in a medial direction relative to the user's patella.

7. The unitary knee patella stabilizer of claim 1, wherein the upper and lower buttress straps are adapted to vary compression around the user's patella by increasing or decreasing tightness of the plurality of straps.

8. The unitary knee patella stabilizer of claim 1, wherein the buttress is adapted to properly align the user's patella.

9. The system of claim 1, wherein the buttress is adapted to vary compression around the user's patella by increasing or decreasing tightness of the upper and lower buttress straps.

10. The system of claim 1, wherein the fasteners comprise Velcro®.

11. The system of claim 1, wherein the patella stabilizer sleeve further comprises:
- a first hinge placed along a medial portion of the patella stabilizer sleeve; and
- a second hinge placed opposite the first hinge.

12. unitary hinged knee support apparatus adapted to accommodate a leg portion of a user, the apparatus comprising:
- an open-upper end and an open-lower end;
- a patella opening;
- an upper fastener assembly having a first strap, connected at its proximal end to an upper end of the apparatus, the first strap having a fastener at a distal end of the first strap;
- a lower fastener assembly having a second strap, connected at its proximal end to a lower end of the apparatus, the second strap having a fastener at a distal end of the second strap;
- a first pair of slots positioned proximate to an interior aspect of the patella opening;
- a second pair of slots positioned proximate to an exterior aspect of the patella opening; and
- the apparatus adapted to receive a buttress comprising an upper strap and a lower strap, the buttress being adapted to be adjustably positioned on an inside surface of the apparatus around a location on a circumferential edge of the patella opening, the first and second pairs of slots are adapted to allow passage of the upper and lower buttress straps therethrough for securement of the buttress to the apparatus thereby allowing positioning of the buttress in at least one of a medial or a lateral direction relative to a user's patella.

13. A method for properly aligning a user's patella, the method comprising:
- providing a unitary knee patella stabilizer having an upper fastener assembly comprising a first strap and a lower fastener assembly comprising a second strap;
- inserting a leg portion of the user through an open-upper end and an open-lower end of the stabilizer;
- securing, via the upper fastener assembly, a thigh region of the user;
- securing, via the lower fastener assembly, a calf region of the user;
- adjustably positioning, on an inside surface of the stabilizer around a location on a circumferential edge of a patella opening, a buttress comprising an upper strap and a lower strap for varying compression around the user's patella by increasing or decreasing tightness of the plurality of straps;
- threading the plurality of straps through at least one of first and second pairs of slots, the first pair of slots positioned proximate to an interior aspect of the patella opening, the second pair of slot positioned proximate to an exterior aspect of the patella opening, the first and second pairs of slots operable to allow positioning of the buttress in at least one of a medial or a lateral direction relative to the user's patella; and
- securing the buttress to the stabilizer via the upper and lower buttress straps.

* * * * *